United States Patent [19]

Ellis et al.

[11] Patent Number: 5,246,000
[45] Date of Patent: Sep. 21, 1993

[54] APPARATUS AND METHOD FOR TESTING THE RESPONSE OF CARDIAC PACEMAKERS TO ELECTROMAGNETIC INTERFERENCE

[75] Inventors: Vincent J. Ellis, Stafford; Charles L. Brown, Manassas, both of Va.

[73] Assignee: The United States of America as represented by the Secretary of the Army, Washington, D.C.

[21] Appl. No.: 874,320

[22] Filed: Apr. 27, 1992

[51] Int. Cl.$^5$ ............................................. A61N 1/362
[52] U.S. Cl. ....................................................... 607/27
[58] Field of Search .............................. 128/419.0 PT

[56] References Cited

U.S. PATENT DOCUMENTS 3,310,885  3/1967  Alderson ................................. 35/17

OTHER PUBLICATIONS

"Pacemaker Standard," Association for the Advancement of Medical Instrumentation (AAMI), Aug. 1965.
Gandhi, et al, "Part-Body and Multibody Effects on Absorption of Radio-Frequency Electromagnetic Energy by Animals and by Models of Man," Radio Science, vol. 14, No. 6S, pp. 15-21, Nov.-Dec. 1979.
Hartsgrove, et al, "Simulated Biological Materials for Electromagnetic Radiation Absorption Studies," Bioelectromagnetic, 8:29-36 (1987).
Bock, T., "EMP Tests of Implantable Cardiac Pacemakers," HDL-PRL-88—3, Mar. 1988.
"Continuous Wave Simulation and Instrumentation System Maintenance and Operation Manual," IRT Corporation, Mar. 1988.
Durney, C., et al, "Radiofrequency Radiation Dosimetry Handbook," USAFSAM-TR-85-73, Oct. 1986.

Primary Examiner—William E. Kamm
Attorney, Agent, or Firm—Saul Elbaum; Jason Shapiro

[57] ABSTRACT

A phantom test cell and method for testing the response of a cardiac pacemaker to electromagnetic fields. The phantom comprises a substantially rigid shell which has a torso-like section and two leg-like appendages. The entire shell is filled with a tissue-equivalent material, which in one embodiment represents an upper bound approximation of human whole body averages. The phantom's torso is equipped with a plurality of access ports to which a current probe containment vessel may attach when immersed in the tissue-equivalent material. The containment vessel houses a current probe and flooded tube through which an implanted pacemaker's leads may pass, allowing induced currents to be monitored. In operation, lead current measurements are taken within the phantom and are normalized using measurements taken without the presence of a phantom. A transfer function is computed by taking the ratio of the induced current measured and a reference E-field and/or H-field measurement. A source of interest is then convolved with the transfer function to determine what the induced current would be in an implanted pacemaker. In one embodiment, the induced current which is arrived at analytically is then physically injected into a cardiac pacemaker outside the test phantom to reproduce EMI effects.

10 Claims, 2 Drawing Sheets

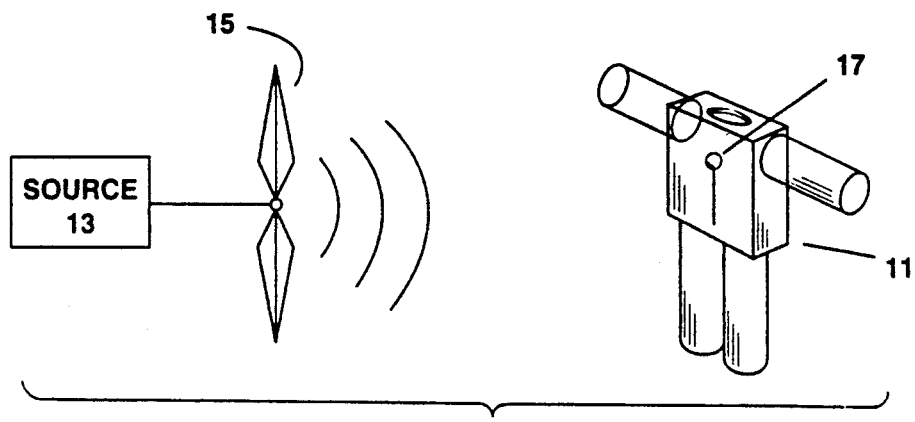
FIG. 1
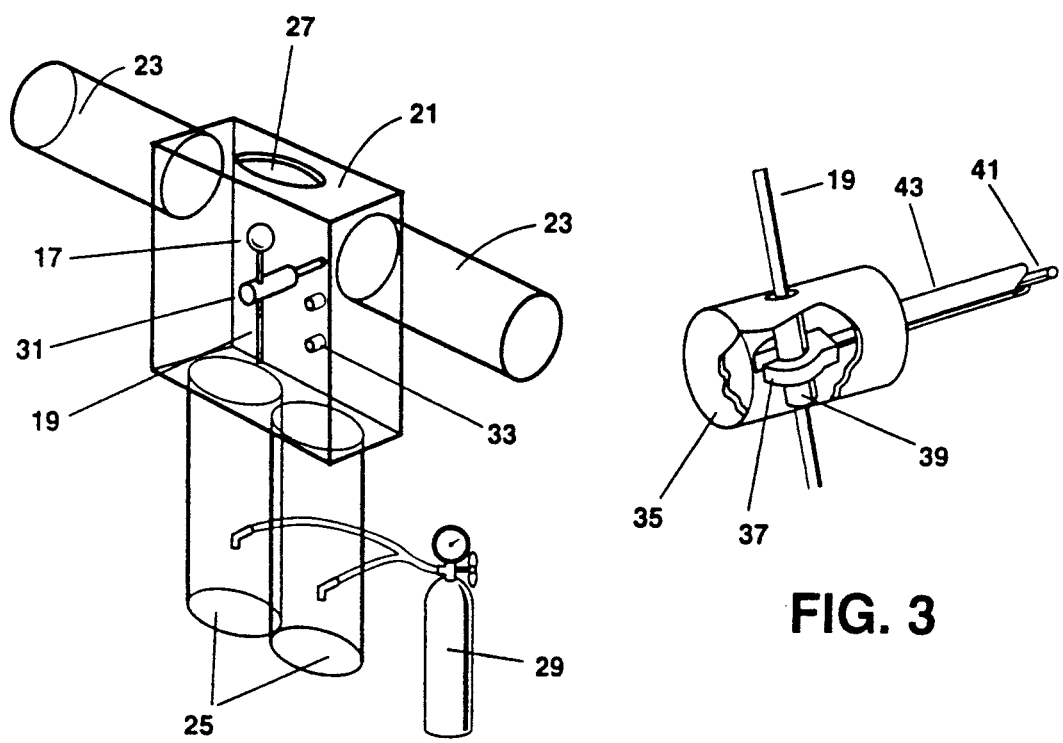
FIG. 2(a)
FIG. 3

APPARATUS AND METHOD FOR TESTING THE RESPONSE OF CARDIAC PACEMAKERS TO ELECTROMAGNETIC INTERFERENCE

GOVERNMENTAL INTEREST

The invention described herein may be manufactured, used and licensed by or for the U.S. Government for governmental purposes without the payment to us of any royalties thereon.

BACKGROUND OF THE INVENTION

The present invention relates to an apparatus and method for evaluating the electrical stress upon, and the response of, an implantable cardiac pacemaker to electromagnetic fields. More particularly, the present invention relates to an apparatus and hybrid method for evaluating the response of an implantable cardiac pacemaker which employs in vitro and bench testing.

Cardiac pacemakers (CPMs) have experienced significant technological advancements over the last decade, evolving from simple and bulky pulse generators to the small computerized units implanted in humans today. With the implementation of sensitive digital electronics in modern pacemaker designs, concerns have been expressed for the possibility of an increased sensitivity of CPMs to electromagnetic interference (EMI). To some extent these concerns have abated due to the increased sensitivity of CPM manufacturers to the EMI problem.

While the intent of the manufacturer may be to protect the CPM wearer from common and frequent sources of EMI, such as power line fields, microwave oven leakage, security system scanners, etc., there are other sources of EMI which should be accounted for in CPM designs. One of these sources of EMI is an electromagnetic pulse (EMP) simulator. Although it would be considered unlikely for the average CPM wearer to be subjected to a simulator's EMP, the effects of EMP on pacemakers is an important consideration for employees at EMP simulator sites, as well as CPM wearers in nearby public areas.

Previous EMI testing of pacemakers consisted of immersing pacemaker test samples in a saline-filled Plexiglas tank and subjecting them to a source of EMI. For EMP testing in particular, a timing circuit was used to fire the EMP within the appropriate pacemaker sense and refractory windows.

A CPM's sense window is a period of time in which the CPM is waiting for a natural heart beat. The refractory window is a period of time in which the CPM is simply waiting between heart beats and is not accepting external input. A CPM is constantly cycling through these windows. If a CPM detects a heart beat in the sense time window, the refractory period starts. If no heart beat is detected in the sense time window, the pacemaker generates a pulse to stimulate the heart, and then the refractory period begins. During a test, the continuous operation of the pacemaker is monitored, and diagnostics are performed before and after each EMI event.

The Association for the Advancement of Medical Instrumentation (AAMI) published in 1975 a "Pacemaker Standard" which specifically called for a rectangular test cell, or "phantom," that basically represents a typical male torso. The phantom was filled with a saline solution of a conductivity believed at the time to be consistent with the conductivity of human tissue at a defined frequency. The standard called for a pacemaker to be immersed in the center of the phantom with the CPM lead in a straight run parallel to the sides of the phantom and parallel to the incident E-field. A constant depth of 1 cm was to be maintained between the CPM lead and the front wall of the phantom.

Although the procedures set forth by the AAMI are consistent with the original objectives of the standard in most ways, they are not completely adequate for testing the effects of all EMI sources. The AAMI phantom does not consider any of the human extremities or surface contours and does not address the effects of the real earth interaction with the phantom and incident EMI.

The interaction of electromagnetic fields with the ground and the interaction of the human body with the ground (in the presence of electromagnetic fields) are important phenomenon for investigation when studying the effects of electromagnetic fields on implanted CPMs. Electromagnetic fields themselves can be attenuated or amplified when reflecting from a ground plane. Furthermore, the response of the human body to an electromagnetic field (.e. the amount of electromagnetic energy absorbed into the body) can be dramatically effected by contact or close proximity to the ground. The AAMI test cell was designed to be used in a free-field test scenario, and cannot accurately simulate a human standing on the ground for EM effects testing.

The "Pacemaker Standard" also calls for a saline solution with a conductivity of 0.267 S/m to be used as the test cell filler. However, the rationale for the use of this value of conductivity is unclear and appears to be an inappropriate choice for all EMI testing. Maintaining a uniform concentration of solute is another problem associated with filling a phantom with a saline solution.

In addition, the AAMI standard does not offer procedures or describe the apparatus for obtaining electrical stress data (currents and/or voltages on the pacemakers' lead(s)) for a pacemaker under test. Instead, the standard calls for monitoring electrodes to be placed in the test cell medium for the purpose of monitoring the pacemaker's output only, not the immediate electrical stresses input to the pacemaker. These electrodes can only qualitatively indicate the response of the pacemaker to the EM field (i.e. provide information as to whether the EM field had an effect on CPM operation). In order to quantitatively establish the effects of EM fields on pacemakers, electrical stress data must be obtained.

SUMMARY OF THE INVENTION

Accordingly, it is an object of the present invention to provide an apparatus and method for quantitatively evaluating the electrical stress upon, and the response of, an implanted cardiac pacemaker to an electromagnetic field.

It is another object of the present invention to provide an apparatus and method for quantitatively evaluating the susceptibility and performance of an implanted cardiac pacemaker exposed to an electromagnetic field in the presence of ground plane effects, and which accounts for human extremities.

It is still another object of the present invention to provide an apparatus and method for quantitatively evaluating the susceptibility and performance of an implanted cardiac pacemaker exposed to an electromagnetic field which uses a saline solution with a conductivity that is an upper bound representation of the whole body average conductivity for human tissue.

It is yet another object of the present invention to provide a method for quantitatively evaluating the susceptibility and performance of an implanted cardiac pacemaker exposed to an electromagnetic field which requires a limited number of in vitro measurements, and allows analytical determination of induced current thereafter.

A further object of the present invention is to provide a method for quantitatively evaluating the susceptibility and performance of an implanted cardiac pacemaker exposed to an electromagnetic field which requires a limited number of in vitro measurements and allows bench-top evaluation thereafter.

Still another object of the present invention is to provide an apparatus and method whereby a substantially uniform concentration of solute is maintained in a phantom for use in evaluating the performance of an implanted cardiac pacemaker exposed to an electromagnetic field.

These objects and others not specifically enumerated are accomplished by first generating an electromagnetic field, varying the frequency of the field, and characterizing it over the frequency range of interest. Then, a cardiac pacemaker is placed within a phantom filled with a tissue equivalent material and provided with legs. The phantom and implanted pacemaker are positioned at the same location where the previous field was characterized, and an identical field is generated over the same frequency range. The current induced in the pacemaker lead is measured and recorded to obtain the frequency domain transfer function. Outside the test cell, a source of interest is then convolved with the transfer function to determine what current, or stress, would be produced. In one embodiment, the current arrived at using such a method is then injected into an equivalent circuit, and the voltage output of a free standing pacemaker is monitored to determine the effect upon an implanted pacemaker of the same type. In another embodiment, the method includes the introduction of gas near the base of the phantom to agitate the filler solution thereby achieving a substantially uniform concentration of solute and improving reliability and repeatability.

BRIEF DESCRIPTION OF THE DRAWINGS

The preferred embodiments of the present invention will be described with reference to the accompanying drawings in which:

FIG. 1 is a schematic illustration of the in vitro test components;

FIG. 2a is a cut-away view of a vertical phantom showing the location of an "implanted" CPM and the probe assembly;

FIG. 3 is a cut-away view of the probe assembly; and

DESCRIPTION OF THE PREFERRED EMBODIMENTS

Turning now to FIG. 1, a cardiac pacemaker (CPM) 17 is shown within a vertically oriented phantom 11 according to the present invention. A source of electromagnetic radiation 13 and an antenna 15 are used to create an electromagnetic field which is made to propagate toward, and interact with, the phantom 11. The location of the CPM 17 within the phantom 11 and in relation to the antenna 15 is determined prior to testing and corresponds to a point in space where the electromagnetic field produced in the absence of the phantom 11 has been fully characterized in three orthogonal directions.

Figure 2B:
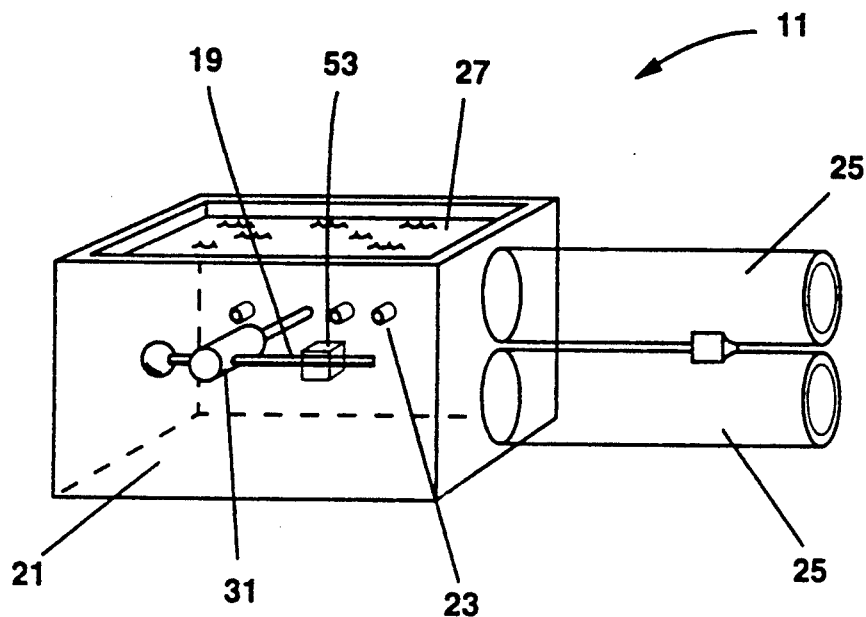
FIG. 2b is a cut-away view of a horizontal phantom showing the location of an "implanted" CPM and the probe assembly.

FIGS. 2(a) and 2(b) depicts a phantom according to the present invention, which comprises a torso 21 and legs 25 which are substantially rigid and filled with a tissue-equivalent material 27. When the phantom 11 is used in a vertical position it is also provided with arm-like appendages 23 to better approximate a human signature. No arms 23 are provided for tests in which the phantom 11 is laid on its side (not shown). The phantom 21 should be constructed of a material which exhibits little electromagnetic attenuation. A preferred material for this purpose is an acrylic plastic.

For ease of manufacture, reasonable accuracy, and the least possible divergence from AAMI standards, the phantom torso 21 is preferably constructed as a rectangular tank. For greater accuracy an ellipsoidal shape may be used. A top or side opening in the torso 21 is provided for purposes of filling the phantom 11 and for access to the CPM 17 and probe containment vessel 31. The location of the opening depends on whether the phantom is to be used in a vertical or horizontal position. In either case, the phantom 11 is typically provided with two capped cylinders which serve as legs 25. The presence of the legs 25 is necessary to account for ground plane interactions which may affect CPM performance. Even when the phantom 11 is positioned horizontally with respect to the ground plane (and without arms 23), the presence of legs 25 affects the way the body couples with the field and are thus thought to be necessary for a quantitative evaluation of CPM response to EMI. When arms 23 are provided to increase the horizontal profile of the phantom 11 they are also in the form of capped cylinders.

The filler material 27 is chosen to simulate the electrical properties of specific tissues over the frequency range of interest, which for EMP testing is between 10 kHz and 200 MHz. Currently, no material has been developed which can accurately simulate the electrical properties of all body tissues over a wide range of frequencies. One approach has been to take a whole body average (WBA) of tissue conductivity and permittivity, and to chose a filler material with corresponding values. No material, however, has been identified which can accurately simulate WBA parameters over the wide frequency ranges.

The present invention resolves this problem by using a saline solution as a filler material 27 and specifying a conductivity which is an upper bound representation of the WBA conductivity for human tissue at the frequencies of interest. Over the frequency range of 10 kHz to 200 MHz, the conductivity of the human body varies from 0.08 siemens per meter (S/m) to 0.544 S/m, and the relative permittivity varies from $42 \times 10^3$ to 45.9. Since body resonances occur between 30 and 80 MHz, values for the electrical parameters were chosen in this range to provide a reasonable upper bound. It is preferred that the filler material 27 be comprised of a saline solution having a conductivity of 0.45 S/m (approximately 0.03 molar NaCl), which approximates WBA values for human tissue at the upper end of the resonant frequencies. The relative permittivity of the saline solution in this range is about 80, which is reasonably close to the resonant permittivity of human body tissues, whose WBA is about 55. Additionally, a permittivity of 80 in this frequency range equates approximately to that of human muscle tissue. It should be noted that the AAMI "Pacemaker Standard" calls for a saline solution with a conductivity of 0.267 S/m to be used as the test cell filler, however, the rationale for such a choice is unclear.

In one embodiment, the CPM 17 is held in place by a series of rectangular bosses 53 which ar provided with vertical through-holes and attached on one side to the inside wall of the front of the phantom torso 21. The CPM lead cable passes through the vertical throughholes but is exposed in the region between any two bosses 53. The CPM 17 rests atop any one of the bosses 53 and is thereby positioned.

A common configuration which is consistent with AAMI standards places the CPM 17 a distance of 1.0 cm from the front wall of the phantom torso 21. The pacemaker lead cable 19 then runs through the bosses 53 and parallel to the major (long) axis of the phantom 11. To thread a pacemaker lead 19 through the holes in the bosses 53, a piece of fishing line is prethreaded through the standoffs from the bottom-most boss 53 to the top-most boss 53 (i.e. opposite the way a pacemaker lead 19 would be threaded). The fishing line is then tied to the pacemaker lead 19 and pulled at the other end. Of course, other means of attachment are possible and the present invention is not meant to be limited to the use of bosses 53 exclusively.

In order to obtain electrical stress data, it is necessary to monitor the current carried in the CPM lead cable 19. As mentioned previously, portions of the cable 19 are accessible in the regions between bosses 53, and it is at these points that a clip-on current probe 37 is attached. The probe 37, however, must operate in a dry environment, so it is encased in a probe containment vessel 31 as shown in FIG. 3.

The probe containment vessel 31 comprises a water=proof housing 35 and probe lead tube 43. In addition, a tubular sheath 39 is made to pass through the center of the housing 35, and is bonded to the outer surface of the housing 35 thereby providing a tunnel which is flooded by the filler material 27, and through which the CPM lead cable 19 may pass. The clip-on current probe 37 is disposed within the housing 35 and around the dry side of the tubular sheath 39. The current probe leads 41 exit the housing 35 through a hole at one end which leads into the probe lead tube 43. The open end of the probe lead tube 43, in turn, fits over one of a series of nipples 33 which protrude into the phantom 11 from the back side of the phantom torso 21 and allow exterior access to the probe leads 41. Those nipples 33 which are not in use are plugged to prevent discharge of the filler material 27.

The probe containment vessel 31 may be constructed of any material which is substantially water-proof and which causes little or no EM attenuation (i.e. about 1 dB or less at the test frequency). In a preferred embodiment, the housing 35 is a hollow Plexiglas cylinder provided with a bonded cover of the same material at one end, and internal threads at the other. A threaded cap with an outward nipple and an O-ring is then used to seal the housing 35 once the current probe 37 has been positioned around the tubular sheath 39. The sheath 39 and threaded cover are also fabricated from Plexiglas or a similar material.

In one embodiment, the probe lead tube 43 comprises flexible tubing, such as TYGON, which is slipped over the nipple on the end cap and one of the nipples 33 on the back wall of the phantom torso 21. To counteract the buoyancy of the probe containment vessel 31, a weight may be disposed within the housing 35, or the vessel 31 positioned beneath one of the bosses 53 along the front inside wall of the phantom torso 21. In another embodiment, the probe lead tube 43 comprises a substantially rigid tube of a Plexiglas-like material, which is bonded to the housing 35 at one end, and threaded at the other. The nipples 33 in this case are also threaded to receive the tube.

For a five and one half foot tall phantom 11, a 3.0 inch diameter tube is typically employed as the housing 35, a 0.125 diameter tube as the sheath 39, and 0.875 diameter flexible tubing for the current probe lead tube 43. A suitable clip-on current probe 37 is the EG & G model COP-5.

In addition to the foregoing, a phantom 11 according to the present invention may also be provided with means 29 to inject air or some other gas at the base of the legs 25 and one or more drain valves. The introduction of gas near the base of the phantom 11 agitates the filler solution 27 thereby achieving a substantially uniform concentration of solute and improving the repeatability of the test. A suitable mean for injecting the gas includes, but is not limited to, a compressed gas container with regulating means, tubing which is split by a "Y" connector, and a plurality of one-way valves or stopcocks near the base of the phantom 11 to allow egress of the pressurized gas without significant fluid backflow. In practice, the filler solution 27 is agitated continually before and after each set of measurements.

Before testing the EMI-induced response of an implanted pacemaker 17, it is necessary to map the EM fields produced by the source 13 and antenna 15 in the chamber where the tests are to be conducted. Stepped, continuous wave fields are generated over the frequency range of interest. At the same time, the amplitude and orientation of the E and H-fields are determined in three orthogonal directions and at locations corresponding to the future locations of the CPM leads 19 within the phantom All measurements are referenced to a common H-field measurement, denoted $H(jw)_0$, which is preferably taken in the ground plane. In one embodiment, the longitudinal axis of the antenna 15 and the reference location are coplanar at ground, with the reference location being 15 meters from the centerline of the antenna 15 (which is 300 meters long). In this way, all data measurements are normalized to the same source, and variations in output are accounted for.

Two test locations within the chamber should be identified for purposes of placing the phantom 11 in either a vertical or horizontal position relative to the centerline of the antenna 15. The vertical position should be chosen such that unipolar and bipolar CPMs will be excited by vertical E-fields, and a dual lead CPM will be excited by H-fields which are normal to the loop formed by the leads. Unipolar and bipolar CPM leads are typically made to run along the major axis of the phantom 11 to promote E-field coupling. The leads of a dual-lead CPM are preferably made to run in a looped configuration to promote magnetic (H-field) coupling. Current measurements at these locations are denoted $I(jw)_{mard}$. Similarly, electric field measurements are denoted $E(jw)_{mard}$, and magnetic field measurements $H(jw)_{mard}$.

The phantom 11 is placed within the test chamber at the desired location corresponding to a vertical or horizontal orientation. The CPM 17 and CPM leads 19 are positioned precisely at those points where the E and H-fields have bee mapped. Continuous wave fields are generated over the frequency range of interest, as was done in the mapping procedure. Additionally, current measurements are taken with the probe containment vessel 31. The current measurements can be described mathematically as follows:

$$I(jw)_{data} = \frac{I(jw)_{msrd}}{H(jw)_0}.$$

The aforementioned field measurements are described similarly:

$$E(jw)_{data} \cdot H(jw)_{data} = \frac{E(jw)_{msrd} \cdot H(jw)_{msrd}}{H(jw)_0}.$$

Once the current response and field measurements have been collected, it is possible to compute the transfer function (by electronic means for example) which is written:

$$TF(jw) = \frac{I(jw)_{data}}{E(jw)_{data} \cdot H(jw)_{data}} = \frac{I(jw)_{msrd}}{E(jw)_{msrd} \cdot H(jw)_{msrd}}.$$

This makes it possible, in turn, to determine the induced current in an implanted pacemaker at any given frequency and field intensity by analytical, rather than experimental, means.

The response of the system is determined by convolving a source of EMI with the transfer function computed in the last step. Since the procedure described involves the convolution of frequency-domain field waveforms with the appropriate CPM transfer functions to produce the frequency-domain response, it is also possible to perform an inverse Fourier transform on these responses to yield time-domain lead current responses of a CPM exposed to the EMI source.

Figure 4:
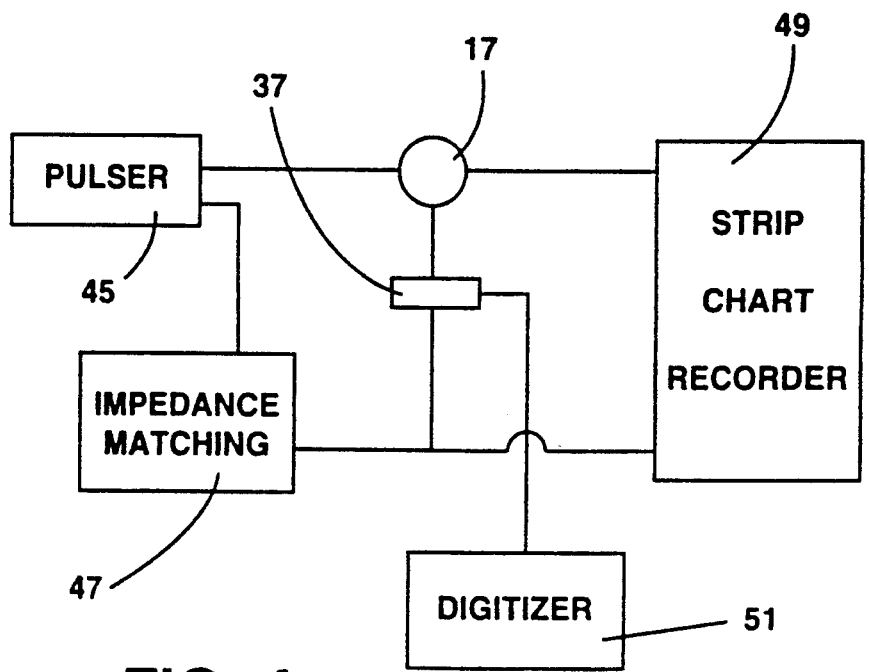
FIG. 4 is a schematic representation of the current injecting technique.

The upper bound currents resulting from analysis of the convolved continuous wave data may be obtained through comparisons of waveform characteristics including maximum slope, peak amplitude, and normalized total energy. It is these upper bound currents that then serve as the output design model for current injection testing, shown schematically in FIG. 4.

Current injection testing consists of three steps per test pulse (current pulse): prediagnostics, the actual test pulse, and post-diagnostics. Prediagnostics is accomplished by recording the CPM 17 program settings and characterizing the normal output of that CPM in terms of voltage, pulse width, and pulse train period.

Before firing an actual test pulse, the CPM 17 is connected to a source pulser 45 and impedance matching device 47 to simulate the induced current arrived at by convolving the real source of interest with the transfer function determined using in vitro techniques. A strip chart recorder 49, or some other functionally equivalent device, is used to monitor the voltage output of the CPM 17 just before, during, and immediately following a test pulse. In addition, a current probe 37 may be used to monitor the CPM lead current directly This information is preferably recorded using a digital storage oscilloscope 51, or some other device which provides a permanent record for examination. Post-diagnostic procedures then mimic the pre-diagnostic procedures described above, and are used to determine if there was a change in CPM functions.

The main advantage of the current injection technique is that it provides quantitative stress data without requiring the use of a phantom test cell 11 Once the necessary transfer functions have been obtained, the response of a given cardiac pacemaker may be evaluated in bench experiments without elaborate instrumentation.

While there has been described and illustrated specific embodiments of the invention, it will be obvious that various changes, modifications and additions can be made herein without departing from the field of the invention which should be limited only by the scope of the appended claims.

We claim:

1. A phantom for testing the response of a cardiac pacemaker to electromagnetic fields, said phantom comprising a substantially rigid shell provided with a torso-like section and two leg-like appendages attached thereto; a tissue-equivalent material disposed within said rigid shell; a plurality of ports disposed along one side of said torso-like section; a probe containment device comprising a water-tight housing, tubular extension, and tubular passage through said housing; a clip-on current probe disposed within said containment device and around said tubular passage; means to connect said tubular extension to any of said ports; and means to position a cardiac pacemaker within said rigid shell such that any leads emanating from said pacemaker are made to pass through said tubular passage.

2. A phantom for testing the response of a cardiac pacemaker to electromagnetic fields, said phantom comprising:
   a substantially rigid shell comprising a rectangular tank and two right circular cylinders, said tank having one open side and a side provided with two holes, said cylinders each having one open end which is attached to said tank concentric with one of said holes;
   a tissue-equivalent material disposed within said shell;
   a plurality of ports along one side of said rectangular tank;
   a probe containment device comprising a water-tight housing, a tubular conduit extending from said housing, and a tubular passage through the center of said housing;
   a clip-on current probe disposed within said containment device and around said tubular passage, said current probe having one or more lead wires, and said lead wires being disposed within and extending from said tubular conduit;
   means to connect said tubular conduit to any of said ports in such a manner as to maintain substantial perpendicularity of said conduit to the side of said rectangular tank which is provided with ports;
   means to hold a cardiac pacemaker within said phantom;
   wherein a pacemaker may be positioned within said phantom, and any leads emanating therefrom can be made to pass through said tubular passage so that induced currents may be monitored at different positions along said pacemaker lead.

3. The invention of claim 2 wherein the open side of said rectangular tank is adjacent to the side provided with said holes, whereby said phantom may be laid such that said right circular cylinders are parallel to the ground plane and said open side will contain said tissue-equivalent material, thereby allowing EMI tests to be conducted in a horizontal position.

4. The invention of claim 2 wherein the open side of said rectangular tank is opposite the side provided with said holes, whereby said phantom may be positioned upon said right circular cylinders allowing EMI tests to be conducted in a vertical position.

5. A phantom for testing the response of a cardiac pacemaker to electromagnetic fields, said phantom comprising:
   a substantially rigid shell comprising a rectangular tank and two right circular cylinders, said tank having one open side and a side provided with two holes, said cylinders each having one open end which is attached to said tank concentric with one of said holes;
   a tissue-equivalent material disposed within said shell, said tissue-equivalent material comprising a saline solution;
   means to introduce gas bubbles near the closed ends of said right circular cylinders to agitate said saline solution;
   a plurality of ports along one side of said rectangular tank;
   a probe containment device comprising a water-tight housing, a tubular conduit extending from said housing, and a tubular passage through the center of said housing;
   a clip-on current probe disposed within said containment device and around said tubular passage, said current probe having one or more lead wires, and said lead wires being disposed within and extending from said tubular conduit;
   means to connect said tubular conduit to any of said ports in such a manner as to maintain substantial perpendicularity of said conduit to the side of said rectangular tank which is provided with ports;
   means to hold a cardiac pacemaker within said phantom;
   wherein a pacemaker may be positioned within said phantom, and any leads emanating therefrom can be made to pass through said tubular passage so that induced currents may be monitored at different positions along said pacemaker lead.

6. The invention of claim 5 wherein said saline solution has a conductivity of 0.45 S/m.

7. A method for testing the response of a cardiac pacemaker to electromagnetic fields, said method comprising the steps of:
   (a) generating an electromagnetic field with a source and an antenna;
   (b) varying the output frequency of said source;
   (c) measuring the amplitude and orientation of the E-field or H-field at a point in space relative to said antenna where the pacemaker is to be positioned during the test, wherein said measurement is taken in such a way as to characterize the field in three coordinate planes and over the frequency range of interest;
   (d) placing the cardiac pacemaker within a phantom comprising a substantially rigid shell filled with a tissue equivalent material, wherein said phantom is provided with leg-like appendages to account for ground plane interaction;
   (e) positioning said phantom so that the center of the pacemaker lead resides at the point in space where previous measurements were taken;
   (f) generating an electromagnetic field as in step (a);
   (g) measuring the induced current in the pacemaker lead over the frequency range of interest;
   (h) computing the transfer function produced by the ratio of the induced current measured and the field characterized in step (c), whereby it is possible to determine the induced current in an implanted pacemaker given any frequency and field intensity by analytical means and without resort to further testing.

8. A method for testing the response of a cardiac pacemaker to electromagnetic fields, said method comprising the steps of:
   (a) generating an electromagnetic field with a source and an antenna;
   (b) varying the output frequency of said source;
   (c) measuring the amplitude and orientation of the E-field or H-field at a point in space relative to said antenna where the pacemaker is to be positioned during the test, wherein said measurement is taken in such a way as to characterize the field in three coordinate planes and over the frequency range of interest;
   (d) placing the cardiac pacemaker within a phantom comprising a substantially rigid shell filled with a tissue equivalent material, wherein said phantom is provided with leg-like appendages to account for ground plane interaction;
   (e) positioning said phantom so that the center of the pacemaker lead resides at the point in space where previous measurements were taken:
   (f) generating an electromagnetic field as in step (a);
   (g) measuring the induced current in the pacemaker lead over the frequency range of interest;
   (h) computing the transfer function produced by the ratio of the induced current measured and the field characterized in step (c);
   (i) convolving a source of interest with said transfer function to determine what the induced current would be in an implanted pacemaker;
   (j) injecting the current arrived at in step (i) into a free-standing pacemaker outside the phantom cavity;
   (k) monitoring the voltage output of said pacemaker to determine the effect of said source on said pacemaker performance, whereby the response of said pacemaker to an arbitrary electromagnetic source while implanted may be evaluated without an actual source or phantom.

9. The method of claims 7 or 8 wherein said phantom is filled with a saline solution and provided with means to introduce gas bubbles at the base of said legs to agitate the solution and achieve a substantially uniform distribution of particles throughout the phantom, thereby improving the accuracy and repeatability of said method.

10. The method of claim 9 wherein said saline solution has a conductivity of 0.45 S/m.

* * * * *